United States Patent [19]

Gorecki et al.

[11] 4,390,526

[45] Jun. 28, 1983

[54] PHARMACEUTICAL AGENTS FOR THE TREATMENT OF SICKLE CELL DISEASE

[75] Inventors: Marian Gorecki; Clemenceau T. A. Acquaye; Meir Wilchek, all of Rehovot, Israel; Alexander Rich, Cambridge, Mass.

[73] Assignee: Yeda Research & Development Co. Ltd., Rehovot, Israel

[21] Appl. No.: 157,107

[22] Filed: Jun. 6, 1980

[30] Foreign Application Priority Data

Jun. 21, 1979 [IL] Israel .......................................... 57609

[51] Int. Cl.$^3$ ............................................. A61K 37/00
[52] U.S. Cl. .................................. 424/177; 424/248.5; 424/248.52; 424/248.53; 424/248.54; 424/248.55; 424/263; 424/273 R; 424/274; 424/275; 424/309; 424/320; 424/324
[58] Field of Search ............... 424/309, 177, 275, 320, 424/248.54, 263, 273, 274, 248.55, 324, 248.5, 248.52, 248.53

[56] References Cited

U.S. PATENT DOCUMENTS

| | | | |
|---|---|---|---|
| 3,466,321 | 9/1969 | Morrew | 560/38 |
| 3,714,228 | 1/1973 | Massie | 560/38 |
| 3,983,138 | 9/1976 | Saari | 424/309 |
| 4,243,819 | 1/1981 | Henrick et al. | 424/309 |

OTHER PUBLICATIONS

Shirahawa et al.-Chem. Abst., vol. 93, (1980), p. 125443y.
Stuetz et al.-Chem. Abst., vol. 82, (1975), p. 156,375e.
Maclaren-Chem. Abst., vol. 77, (1972), p. 34902a.

Primary Examiner—Sam Rosen
Attorney, Agent, or Firm—Browdy and Neimark

[57] ABSTRACT

The present invention relates to novel compounds selected from $R_1$—COO(CH$_2$)$_n$—$R_2$ and

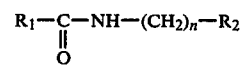

wherein $R_1$ is selected from heterocyclic aromatic and hydrophobic naturally occuring and modified amino acids in the D- and in the L-form, and from peptides, wherein n is an integer of from 1 to 5 and $R_2$ is selected from unsubstituted and substituted phenyl rings, and from heterocyclic rings, as well as to pharmaceutical compositions for preventing sickling of erythrocytes during sickle cell crisis and for desickling of sickle cells of patients afflicted by sickle cell disease, the active ingredient of which is a compound as defined above.

5 Claims, No Drawings

PHARMACEUTICAL AGENTS FOR THE TREATMENT OF SICKLE CELL DISEASE

FIELD OF THE INVENTION

The present invention relates to novel compounds and to pharmaceutical agents which are of value in the treatment of sickle cell disease. The novel pharmaceutical compositions are adapted to prevent sickling of erythrocytes and even to reverse sickling of erythrocytes from persons afflicted by the disease.

BACKGROUND OF THE INVENTION

Sickle cell disease is caused by a haemoglobin mutant called haemoglobin S, hereinafter HbS. The mutation of HbS comprises the replacement of a polar residue, glutamic acid, by a hyrophobic one, valine, in the 6th position of the β-chains, and this renders the HbS capable of polymerization in the desoxy form: see Pauling et al., Science 110, 543 (1949); Ingram:Nature, (London) 178, 792 (1956). In the deoxygenated state the HbS molecules aggregate in the form of elongated microtubular structures which distort the shape of the red cell to a sickle shape. The sickled cells tend to block the blood capillaries and ultimately give rise to the squelae of sickle cell disease.

There are known compounds which affect polymerization of HbS, and there must be made a clear distinction between those which are antisickling agents and those which are antigelling agents.

The antisickling agents are those which are able to pass through the cell membrane of the erythrocytes and prevent or reverse sickling; the latter are those which are adapted to prevent polymerization of deoxygenated HbS, but which do not pass the cell membrane in sufficient quantities and thus are not adapted to prevent or reverse sickling when contacted with red blood cells of a patient suffering from sickle cell disease.

In Table II there is presented a summary of the activity of known compounds, tried for use as antisickling agents, the comparison being on the basis of effective concentrations in vitro. The last item of the Table relates to compounds of the present invention.

Antigelling agents are summarized in Table III. The antigelling agents are not able to prevent sickling nor are they suited to reverse sickling when incubated with erythrocytes.

Sickling cell disease has been studied extensively, but in spite of this there does not exist a universally acceptable therapeutic agent for the treatment of this disease. During recent years attempts have been made to provide such agents. Some of these are based on the use of three types of compounds:

a. Agents which bind covalently with the haemoglobin molecule;
b. Agents which bind non-covalently to this molecule;
c. Agents affecting the cell membrane.

Some of the known antisickling agents have a rather high degree of toxicity, one of these being, for example, potassium cyanate.

According to the present invention there are provided novel active agents for use in the prevention and treatment of sickle cell crises which are both effective and non-toxic.

SUMMARY OF THE INVENTION

The present invention relates to novel compounds for use as active ingredients, along with conventional pharmaceutical excipients, in pharmaceutical compositions for the prevention and/or for the treatment of sickle cell crises. The invention also relates to the pharmaceutical compositions themselves and the method of treatment of sickle cell disease patients using such compounds and composition. The novel compounds inhibit sickling of erythrocytes from sickle cell disease patients, when such cells are incubated together with the novel agents. The antisickling effect is a very pronounced one and the novel agents are effective at low concentrations.

The novel compounds according to the present invention comprise an aromatic compound, such as aromatic amino acid, linked via an ester linkage to an aromatic or heterocyclic alcohol or linked via a peptide bond to an aromatic or heterocyclyc amine. Suitable aromatic amino acids are, for example, D- or L-phenylalanine, tryptophan or tyrosine. A typical effective ester linkage is, for example a carboxy-ester bond. Typical heterocyclic groups when used in the alcohol include thienyl, morpholine, pyridine and pyrrolidone groups.

Amongst typical compounds according to the present invention there may be mentioned L-Phe-OBz.HCl, L-Tyr-OBz.HCl, L-Try-OBz.HCl, L-Pro-OBz.HCl, L-Phe-OBz-(pNO$_2$).HBr, L-Pro-OBz(pNO$_2$).HBr, L-His-OBz(pNO$_2$)-pTs, 1-Ala-L-Phe-OBz.HBr, L-Gly-L-Phe-OBz.HBr, L-Phe-Benzyl amide, L-Val-OBz, L-Leu-OBz, L-Phe-L-Ala-OBz.HBr, L-Try-Lys-OBz.HBr, D-Phe-OBz.HCl, D-Tyr-OBz.HCl, D-Try-OBz.HCl, L-Phe-(2-thienyl)ethyl ester, L-Phe-(2-morpholine)ethyl ester, L-Phe-(2-pyridine)ethyl ester, L-Phe-(2-pyrrolidone)ethyl ester, L-Phe-(2-phenyl)ethyl ester, L-Phe-(3-phenyl)propyl ester, and L-Phe-(4-phenyl)butyl ester. Compounds according to the present invention are adapted to prevent and to reverse sickling of red cells at a concentration as low as about 0.5 to 3 mM when incubated with red blood cells of sickle disease patients. The novel compounds have a very low toxicity. They were tested in mice as regards toxicity. They were found to be non-mutagenic as determined by the Ames method (Ames et al, Mutation Res. 31, 347 (1975)).

DESCRIPTION OF THE PREFERRED EMBODIMENT

The novel compounds according to the present invention comprise in combination an aromatic amino acid linked to an aromatic or heterocyclic alcohol or amine through a carboxylic ester bond or a peptide bond. The novel compound can be designated as benzyl esters of aromatic amino acids and they can be synthesized by reacting such amino acid with phosgene at room temperature in dioxane to form the corresponding N-carboxy anhydride hydrochloride, which latter is reacted with the aromatic alcohol, such as for example C$_6$H$_5$CH$_2$OH to form the desired product in the form of its hydrochloride.

In the present specification and claims, the following abbreviations are used: Alanine (Ala), arginine (Arg), asparagine (Asn), aspartic acid (Asp), cysteine (Cys), glycine (Gly), glutamic acid (Gln), glycine (Gly), histidine (His), isoleucine (Ilu), leucine (Leu), lysine (Lys), methionine (Met), phenylalanine (Phe), proline (Pro), sernine (Ser), threonine (Thr), tryptophan (Trp), tyrosine (Tyr), valine (Val), hydrochloric acid (HCl), benzyl ester (-OBz), and p-toluene sulphonate (pTs).

It is clear that the above method is by illustration only and that various other routes of preparation can be resorted to.

The novel compounds defined above are effective agents for the intended purposes. Further improved compounds which have a lower degree of hydrolysis can be prepared as follows:

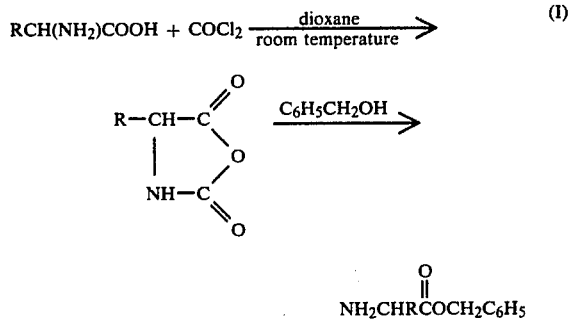

where R is an amino acid residue.

As amino acid there can be used any amino acid listed, or any modification thereof, or any other acid which enhances the product with hydrolysis stability.

Instead of D-Phe, any other aromatic amino acids, or its functional derivative, can be used. The benzene ring can be substituted by conventional substituents such as p-nitro. It is also possible to link the aromatic amino acid to a benzylamine group through a peptide bond.

The compounds set out in Table IV were found to be effective agents for the inhibition of erythrocyte sickling and for the restoration of sickled cells.

The following Examples illustrate the present invention, and these are to be construed in a non-limitative manner.

EXAMPLE 1

Determination of Antigelling Property

The antigelling property of the said new class of compounds was determined by a modified method of Bookchin et al. (1967); (see Bookchin et al, J. Biol. Chem., 242, 248–255, 1967). To 10 μl of a solution of the said new class of compounds in a micro test tube, at about 37° C., 150 μl of 35% of purified HbS were added and vortexed. 15 microliters of a 10% sodium dithionite in 0.05 M phosphate buffer, pH 7.2 were added. The mixture was thoroughly mixed and flushed with nitrogen and quickly stoppered. The micro test tube was incubated at 37° C. for 30 minutes and then transferred to 0° C. for 10 minutes and then returned to 37° C. for 30 minutes. A compound was defined as having antigelling properties when the HbS inhibition mixture remained in the fluid state for a period of more than 20 minutes at 37° C. In the control experiment the inhibitor was omitted and this resulted in gelation within 2 minutes of incubation at 37° C.

The novel agents were found to have an antigelling property. D- and L-Phe-OBz inhibited gelation of HbS at 6 moles to one mole HbS while L-Try-OBz inhibited gelation at 4 moles to one mole of HbS.

L-Lys-L-Phe-L-Phe which had previously been found to have antigelling activity was used as reference standard. It inhibited gelation at 15 moles L-Lys-L-Phe-L-Phe to one mole of HbS.

EXAMPLE 2

Inhibition of Sickling

A venous blood sample was obtained from the anticubital vein of a sickle cell disease patient and washed several times with phosphate buffer saline, pH 7.2, consisting of 145.4 mM NaCl, 4.0 mM KCl, 1.65 mM $Na_2HPO_4$, 0.16 mM $KH_2PO_4$, 0.01 mM $MgCl_2$ and 11.1 mM glucose. The buffy coats were removed by aspiration. To a 300 μl portion of a 20 percent cell suspension, a solution of a compound of the invention was added to give a final concentration of 0.5, 1.5 and 3 mM. The mixture was well stoppered, incubated at 37° C. and swirled at about 100 cycles per minute in a controlled environment incubator. The standard control consisted of a 300 μl of a 20% cell suspension in the buffer in which the novel compound was dissolved. After an incubation period, 20 μl of the treated cell suspension was deoxygenated with 20 μl of 2.0% sodium metabisulphite or with nitrogen gas and examined with a Zeiss microscope.

The shape of the cells, as seen under a Zeiss microscope, are the same as oxygenated untreated cells. The control cells, deoxygenated and untreated with the novel compounds are completely sickled.

EXAMPLE 3

Reversal of Sickling

A sickle cell suspension prepared by the method described in Example 2 was completely deoxygenated by mixing with an equal volume of 2.0% sodium metabisulphite and incubation at 37° C. for 10 minutes. The cells were centrifuged and resuspended in phosphate buffer saline, (see Example 1). A drop of the sickled cells were examined under a Zeiss microscope to ascertain complete sickling.

A solution of a compound of the invention was added to give a final concentration of 3.0 mM. The mixture was flushed with nitrogen gas, incubated at 37° C. and swirled at about 100 cycles per minute in a controlled environment incubator. The control sample consisted of a mixture of 1.0 ml of buffer and 1.0 ml of sickled cells.

A 5 μl aliquot was removed from both the treated cells and a control sample and examined with the Zeiss microscope.

The desickling process was observed within 10 minutes of incubation and completed within 30 minutes of incubation of the sickled cells with the novel class of compounds. The shapes of the erythrocytes as seen under a Zeiss microscope are the same as oxygenated cells.

EXAMPLE 4

Transport of the novel compounds into erythrocytes

As sickle cell disease is caused by a defect of the erythrocytes, in order to study transport of a therapeutic agent for the treatment of the disease into erythrocytes, erythrocytes and no other cells must be used for the transport studies.

Washed erythrocytes were prepared by the method described in Example 2 and used for transport studies. The novel class of compounds were radioactively labelled, using for example, $[^{14}C]$-L-Phe.

The results indicate that the novel compounds, as exemplified by L-Phe-OBz are rapidly transported into erythrocytes by a carrier mediated process as shown by a simple Michaelis plot with a Michaelis constant for transport of 0.175 mM. Time course experiment shows that L-Phe-OBz is rapidly transported into erythrocytes, see Table I.

TABLE I

INCORPORATION OF [$^{14}$C]-L-Phe INTO ERYTHROCYTES

| TIME | PERCENT OF INCORPORATION |
|---|---|
| 0 | 0 |
| 10 | 30 |
| 20 | 70 |
| 30 | 90 |
| 45 | 100 |
| 60 | 90 |

TABLE II

Antisickling Agents. Effective Concentration In Vitro

| Antisickling Agent | Effective Concentration | Reference |
|---|---|---|
| DL—Glyceraldehyde | 20 mM | Nigen, A.M. and Manning J.M. Proc. Natl. Acad. Sci. (USA) 74, 367, 1977. |
| Various Aldehydes and Ketones | 5 mM | Zaugg, R.H.; Walder, J.A.; and Klotz, I.M., J. Biol. Chem. 252, 8548, 1977. |
| Alkyl Urea and Urea | 100 mM | Elbaum, D.; Roth E.F. Jr.; Neumann, G.; Gaffe, E.; Bookchin, R.M.; and Nagel, R.L., Blood, 48, 273, 1976. |
| 2(Benzoyl amino) pyridinium benzoate | 50 mM | Adhikary, P.K; Haynes, J.K.; Patthey, H.L.; and Rhodes, R.S. Experientia, 34, 804, 1978. |
| Dibromo aspirin | 5 mM | Walder, J.A.; Zaugg, R.H.; Iwaoka, R.S.; Watkin, W.G.; and Klotz, I.W., Proc. Acad. Sci. (USA) 74, 5499, 1977. |
| 3,4-dihydro-2,2-dimethyl 2H-1 Benzopyridirium-6-butyric acid | 10 mM | Ekong, D.E.U.; Okogun, J.I.; Enyenihi, V.U.; Belgh-Nairm, V; Nakanishi, K; and Natt, C.; Nature (London) 258, 743, 1975. |
| Pyridoxal | 20 mM | Kark, J.A.; Kale, M.P.; Tarassoff, P.G.; Woods, M.; Lessin, L.S. and Hicks, C.U., J. Chim. Invest., 62, 888, 1978. |
| Cystamine | 220 mM | Hassan, W.; Benzard Y Rosa J, Proc. Natl.Acad. Sci.(USA), 73, 3288, 1976. |
| Nitrogen Mustard | 10 mM | Roth, E. Jr.; Nagel, L.R.; and Bookchin, R.M., Biochem. Biophys, Res. Comm., 48, 612, 1972. |
| Potassium Cyanate | 100 mM | Cerami, A.; and Manning, J.M., Proc. Natl. Acad. Sci., 68, 1180,1971. |
| Dimethyl Adipi- | 10 mM | Lubin, B.L.; Pena, V.; Mentzer, |

TABLE II-continued

Antisickling Agents. Effective Concentration In Vitro

| Antisickling Agent | Effective Concentration | Reference |
|---|---|---|
| midate | | W.C.; Bynum, E.; Parker, L., Proc. Natl. Acad. (USA) 72, 43, 1975. |
| Benzyl esters of some Amino Acids | 0.5–3.0 mM | This invention. |

TABLE III

Antigelling Agents

| Antigelling Agent | Examples | Reference |
|---|---|---|
| Tri- and tetrapeptides | L—Phe—L—Phe—Arg | Votano, J.R.; Gorecki, M.; Rich, A, Science, 196, 1216, 1977. |
| Aromatic compounds | Benzyl alcohol | Ross, P.D. and Subramanian, S. Biochem. Biophys. Res. Comm. 77, 1217, 1977. |
| Aromatic amino acids | L—Phe L—Tyr | Noguchi, C.T. and Schechter, A.N., Biochem, Biophys. Res. Res. Comm. 74, 637,1977. |
| Aromatic amino acids and peptides | L—Phe | Noguchi, C.T. and Schechter, A.N., Biochemistry, 17, 5455, 1977. |
| Oligopeptides that mimic segments of the amino acid sequence of HbS | Val—His—Leu—Thr—Pro—Proc. Natl. Acad. Sci. (USA) | Kubota, S. and Yank, L.T. 74, 5431, 1977. |

TABLE IV

Compounds Active as Antisickling Agents

| | Percentage of Normal Cells |
|---|---|
| 1. L—Phe—OBz.HCl | 90 |
| 2. *L—Tyr—OBz.HCl | 70 |
| 3. *L—Try—OBz.HCl | 95 |
| 4. L—Pro—OBz.HCl | 60 |
| 5. L—Phe—OMe | 0 |
| 6. L—Phe—OBz (pNO$_2$).HBr | 90 |
| 7. L—Pro—OBz (pNO$_2$).HBr | 80 |
| 8. L—His—OBz (pNO$_2$) pTS | 70 |
| 9. L—Ala—L—Phe—OBz.HBr | 90 |
| 10. L—Gly—L—Phe—OBz.HBr | 90 |
| 11. L—Phe—Benzyl amide | 70 |
| 12. L—Val—OBz | 50 |
| 13. L—Leu—OBz | 55 |
| 14. L—Phe—L—Ala—OBz.HBr | 70 |
| 15. L—Try—Lys—OBz.HBr | 70 |
| 16. D—Phe—OBz.HCl | 90 |
| 17. L—Tyr—O Octadecyl.HCl | 10 |
| 18. L—Phe | 0 |

*0.5 mM of compound was used for the incubation of cells.

Erythrocytes were incubated with 3 mM of the compound, and tested for 30 minutes. They were deoxygenated with sodium metabisulphite and examined under a Zeiss microscope.

Compounds No. 5, 17 and 18 are included for comparison and are not part of the invention.

We claim:

1. A pharmaceutical composition for preventing the sickling of erythrocytes during sickle cell crises, and for desickling of sickle cells of patients afflicted by sickle cell disease, comprising a pharmaceutical excipient, and, as active ingredient, an effective amount of the formula

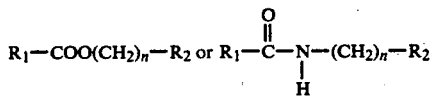

wherein
R₁ is a residue selected from the group consisting of naturally occurring and modified amino acids and from peptides containing said amino acids;
n is an integer of 1 to 5; and
R₂ is selected from the group consisting of unsubstituted thienyl, morpholine, pyridine, and pyrrolidone rings.

2. A composition in accordance with claim 1, wherein said active ingredient is L-Phe-(2-thienyl)ethyl ester, L-Phe-(2-morpholine)ethyl ester, L-Phe-(2-pyridine)ethyl ester, or L-Phe-(2-pyrrolidone)ethyl ester.

3. A method for preventing the sickling of erythrocytes during sickle cell crises, and for desickling of sickle cells of patients afflicted by sickle cell disease, comprising administering to such patients an effective amount of a compound of the formula

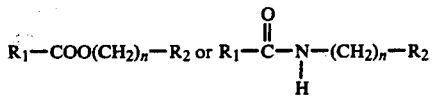

wherein
R₁ is a residue selected from the group consisting of naturally occurring and modified amino acids and from peptides containing said amino acids;
n is an integer of 1 to 5; and
R₂ is selected from the group consisting of unsubstituted or para-nitro substituted phenyl, thienyl, morpholine, pyridine and pyrrolidone rings.

4. A method in accordance with claim 3, wherein said compound is a benzyl ester and the moiety R₁ is selected from the group consisting of phenylalanine, tyrosine, thyroxine, tryptophan, proline, hydroproline, histidine, and from peptides containing such residue.

5. A method in accordance with claim 3, wherein said compound is selected from the group consisting of L-Phe-OBz.HCl, L-Tyr-OBz.HCl, L-Try-OBz.HCl, L-Pro-OBz.HCl, L-Phe-OBz-(pNO₂).HBr, L-Pro-OBz(pNO₂).HBr, L-His-OBz(pNO₂)-pTs, L-Ala-L-Phe-OBz.HBr, L-Gly-L-Phe-OBz.HBr, L-Phe-Benzyl amide, L-Val-OBz, L-Leu-OBz, L-Phe-L-Ala-OBz.HBr, L-Try-Lys-OBz.HBr, D-Phe-OBz.HCl, D-Tyr-OBz.HCl, D-Try-OBz.HCl, L-Phe-(2-thienyl)ethyl ester, L-Phe-(2-morpholine)ethyl ester, L-Phe-(2-pyridine)ethyl ester, L-Phe-(2-pyrrolidone)ethyl ester, L-Phe-(2-phenyl)ethyl ester, L-Phe-(3-phenyl)propyl ester, and L-Phe-(4-phenyl)butyl ester.

* * * * *